United States Patent [19]

Labuz et al.

[11] Patent Number: 5,063,785
[45] Date of Patent: Nov. 12, 1991

[54] PLANE-STRAIN APPARATUS

[75] Inventors: Joseph F. Labuz, St. Paul, Minn.; Ioannis G. Vardoulakis, Athens, Greece; Andrew Drescher, New Brighton, Minn.

[73] Assignee: Regents of the University of Minnesota, Minneapolis, Minn.

[21] Appl. No.: 564,056

[22] Filed: Aug. 7, 1990

[51] Int. Cl.$^5$ .............................................. G01N 3/08
[52] U.S. Cl. .................................................... 73/821
[58] Field of Search ............................. 73/818–825, 73/813, 841, 842, 845, 846, 815, 801, 803

[56] References Cited

U.S. PATENT DOCUMENTS

| | | | |
|---|---|---|---|
| 2,414,550 | 1/1947 | Patch | 73/803 |
| 2,810,289 | 10/1957 | Button | 73/823 |
| 4,009,463 | 2/1977 | Vercellotti et al. | 73/801 |
| 4,825,700 | 5/1989 | Vardoulakis et al. | 73/794 |
| 4,850,231 | 7/1989 | Ralfs et al. | 73/818 |
| 4,854,175 | 8/1989 | Budhu | 73/841 |
| 4,885,941 | 12/1989 | Vardoulakis et al. | 73/794 |

FOREIGN PATENT DOCUMENTS

| | | | |
|---|---|---|---|
| 1516858 | 10/1989 | U.S.S.R. | 73/818 |
| 993829 | 6/1965 | United Kingdom | 73/803 |

Primary Examiner—Robert Raevis
Attorney, Agent, or Firm—Kinney & Lange

[57] ABSTRACT

A plane-strain apparatus is provided for testing soft rock and concrete specimens for failure under compression load in a direction generally along a central axis of the specimen. The specimen has first and second end surfaces, and four side surfaces, which form a generally rectangular prism cross-section configuration. The apparatus includes a bottom support plate supporting the first end surface, and a top plate for loading the second end surface. A frame surrounds the specimen and supports a pair of diametrically opposite base wedge plates aligned with two opposite side surfaces of the specimen. The frame is spaced from the specimen and the base wedges and mating adjustable wedge plates which engage the opposite surfaces of the specimen facing the base wedge plates. The cylindrical frame, and the base wedges and mating adjustment wedge plates restrain movement of the opposite side surfaces of the specimen to be tested in first lateral directions perpendicular to the axis of loading. The specimen is substantially unrestrained from shifting in directions parallel to the adjustable wedge plates. A mechanism for loading the specimen is provided at the second end surface. The applied load is directed by the top plate toward the support plate until the specimen fails in shear and at least two portions of such specimen shifts in a direction parallel to the side plates. Low friction linear slide mechanism is provided for mounting the top plate for movement along a linear support substantially parallel to the plates of the wedges.

18 Claims, 6 Drawing Sheets

PLANE-STRAIN APPARATUS

The invention described herein was made in the course of work under Grant MSS-8906185 from the National Science Foundation. The U.S. Government has certain rights in this invention.

BACKGROUND OF THE INVENTION

The present invention relates to a plane strain detection apparatus which permits testing samples of soft rock or concrete which have an unconfined compressive strength of less than 35 MPa, under axial loads while continuously monitoring the axial force, axial and lateral displacements and translation of a top support plate supporting the sample.

Biaxial testing of geomaterial, which is defined as including, but not limited to, soil, sand, rock, ceramics, concrete, snow and ice, has been recognized as important in determination of geomaterial characteristics. Patents that describe biaxial geomaterial test systems for soils, etc., include Vardoulakis et al U.S. Pat. No. 4,825,700 and Vardoulakis et al U.S. Pat. No. 4,885,941 which is a continuation of Vardoulakis '700. The Vardoulakis '700 and '941 patents describe a biaxial compression test apparatus for geomaterial samples (for soils, etc.) that is designed to allow shear band formation and provide measurements of the stress displacement characteristics of the failure zone. The geomaterial is formed into a right rectangular prism and is surrounded by a elastomeric membrane and is supported by walls along two parallel faces. An axial load is applied while a bottom support plate is horizontally guided by a linear bearing that is substantially friction free. The surfaces in contact with the specimen are glass lined and lubricated. The load is applied to one end of the specimen and load cells provide accurate measurement of the axial force and any eccentricities thereof, as well as friction along the side walls. Displacement transducers monitor the axial and lateral displacements of the specimen and the horizontal movement of the bottom support plate.

SUMMARY OF THE INVENTION

A plane-strain apparatus is provided for testing soft rock and concrete specimens for failure under compression load in a direction generally along a central axis of the specimen. The specimen has first and second end surfaces, and four side surfaces, which form a generally rectangular prism cross section configuration. The plane strain apparatus includes a bottom support plate supporting the first end surface of the specimen, and a top plate for loading the second end surface of the specimen. A pair of bearing plates engage opposite side surfaces of the specimen. A peripheral frame surrounds the specimen and the plates which engage the specimen. The frame is spaced from the specimen and supports a pair of diametrically opposite base wedge plates aligned with the bearing plates on the opposite side surfaces of the specimen. A pair of mating adjustable wedge plates are provided between the base wedge plates and the bearing plates. The frame, the base wedge plates, the mating adjustable wedge plates and the bearing plates restrain movement of opposite side surfaces of the specimen to be tested in first lateral directions perpendicular to the axis of loading.

The specimen is substantially unrestrained from shifting in directions parallel to the adjustable wedge plates. Means for loading the specimen are provided at the second end surface. The applied load is directed by the top plate toward the support plate along a central axis of the specimen until the specimen fails in shear and at least two portions of such specimen shifts in a direction parallel to the side plates.

A pair of bearing plates are placed against the two opposite side surfaces of the specimen that are restrained by the wedge plates and frame. The two portions of the specimen which shift in a direction parallel to the side plates are enclosed within a elastomeric membrane. The adjustable wedge plates are situated between the base plates and the bearing plates.

In the preferred embodiment, the apparatus includes a low friction linear slide means for mounting the top plate for movement along a linear support substantially parallel to the planes of the side plates. This lack of restraint permits lateral shifting of the top plate relative to the bottom support plate when shear failure of the specimen occurs. The apparatus also includes a first displacement sensor means for sensing displacements of the top plate along the axis of the linear slide means. A second linear displacement means is provided which engages at least one of the unrestrained side surface of a specimen to be tested at two different axially spaced locations to determine differential movements between at least two portions of a specimen being tested as it fails. In addition, a third displacement sensing means may be provided for measuring the displacement of the support plate along the support axis.

A lower load cell preferably supports the bottom support plate for measuring the load on the specimen transferred to the bottom support plate. A primary load cell measures the load applied to the first end of a specimen being tested and the difference between the indicated loads on the load cells is an indication of the friction that is present between the specimen and the bearing plates.

In addition, a pressure vessel preferably surrounds the apparatus whereby the pressure vessel is filled with liquid and placed under a pressure.

DETAILED DESCRIPTION OF THE PREFERRED EMBODIMENTS

Figure 1:
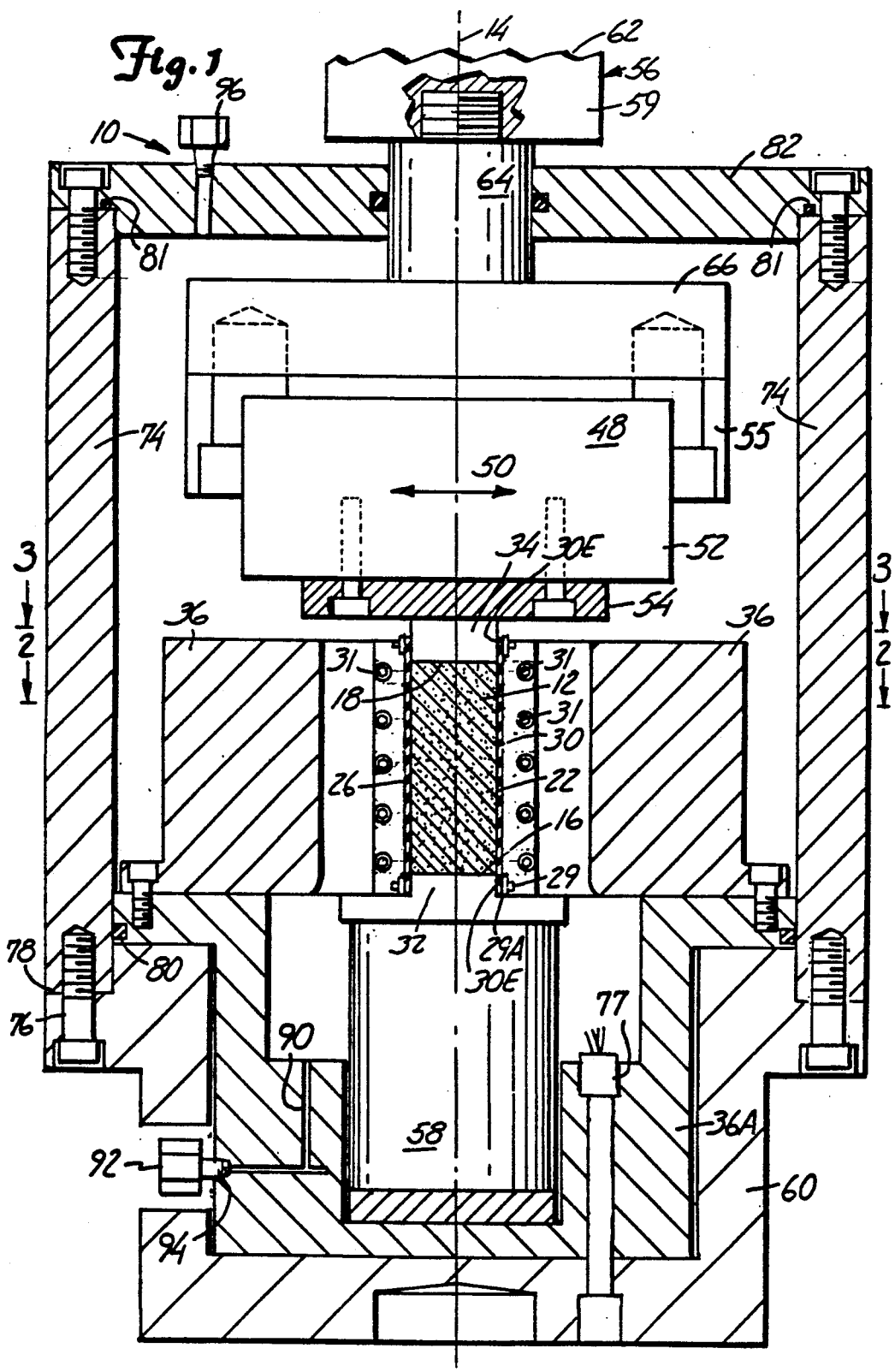
FIG. 1 is a vertical sectional view of a plane strain apparatus made according to the present invention.

A plane-strain apparatus of the present invention is indicated generally at 10 in FIG. 1. The plane-strain apparatus 10 is provided for testing soft rock and concrete specimens 12 for failure under compressive load acting in a direction generally along a central axis 14 of the specimen 12. Soft rock and concrete is defined as that rock and concrete which have an unconfined compressive strength of less than 35 MPa.

The specimen 12 includes first and second end surfaces 16, 18 and four side surfaces, indicated generally at 20, 22, 24 and 26, which form a generally rectangular prism cross section configuration.

The specimen is mounted by placing a pair of bearing plates 28 directly against the two opposite side surfaces 20, 24. The bearing plates will be discussed in detail later.

Figure 5:
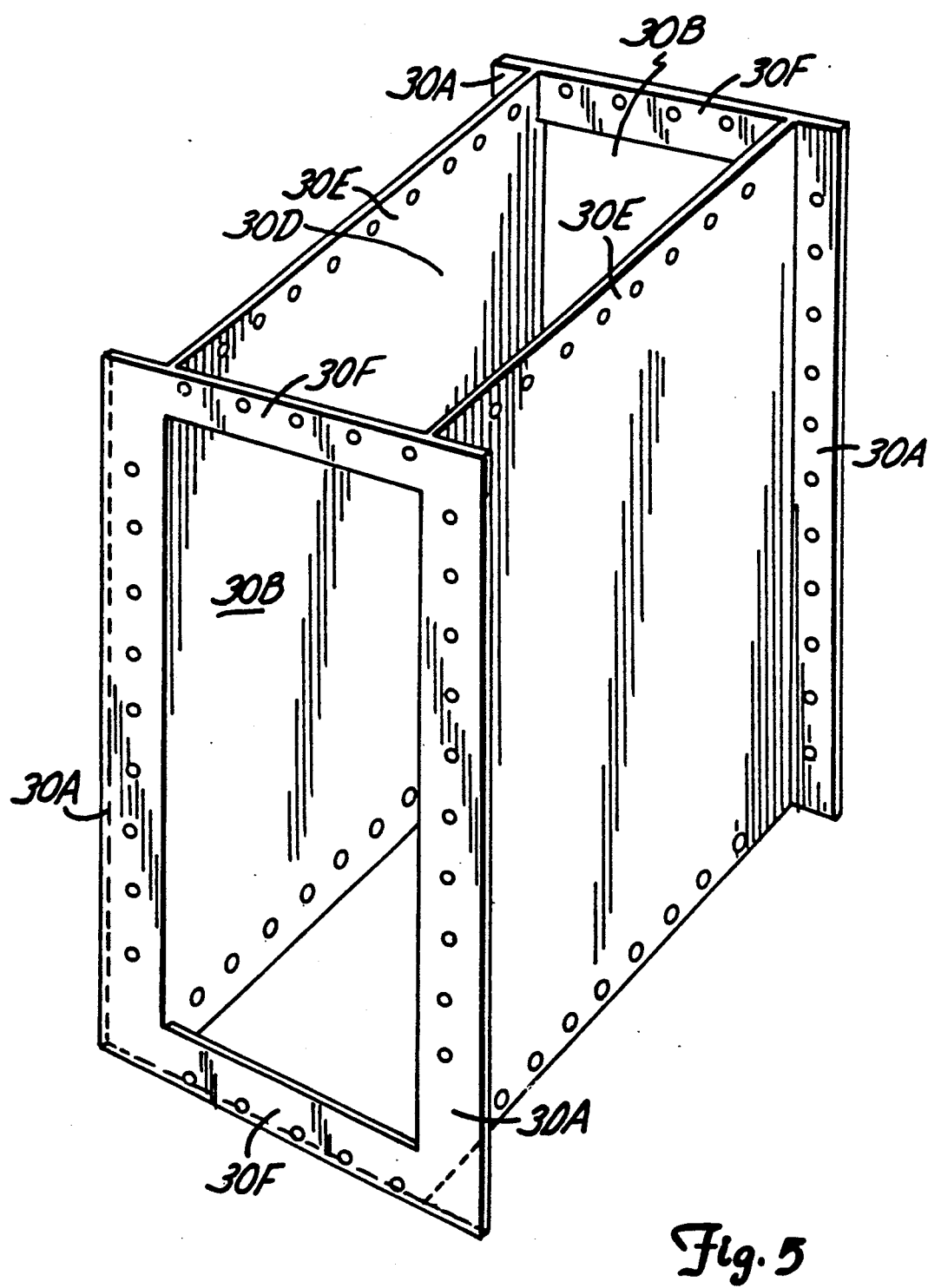
FIG. 5 is a schematic perspective view of a rubber sleeve used for enclosing a specimen.

A bottom support plate 32 and a top plate 34 directly engage the surfaces 16 and 18 of the specimen, respectively. In order to isolate the specimen from fluids used in a test sequence, a elastomeric sleeve or membrane 30, best illustrated in FIG. 5 is placed over the specimen, so the sleeve engages side surfaces 22 and 26, which remain unsupported during test and the sleeve 30 is then sealed on the end plates 32, 34 and bearing plates 28. This provides fluid isolation while allowing direct contact of the loading and restraining members with the respective specimen surfaces.

As illustrated in FIG. 5, the sleeve is left open with openings 30B at side surfaces 20 and 24, so the bearing plates 28 may engage these side surfaces. Peripheral flanges 30A are integrally formed as part of the sleeve 30 and extend outwardly from the specimen to rest on surfaces of the bearing plates 28 surrounding the specimen. A clamp strap 35 is mounted over each of the flaps 30A and screws 31 clamp the strap 35 against the flaps 30A after the membrane is stretched taut. The clamping straps seal the membrane around the specimen sides 20 and 24 and against the side surfaces 22, 26. The straps 35 can be made in section with a gap between two sections to permit shifting of the specimen 12 when the specimen 12 is loaded.

Figure 2:
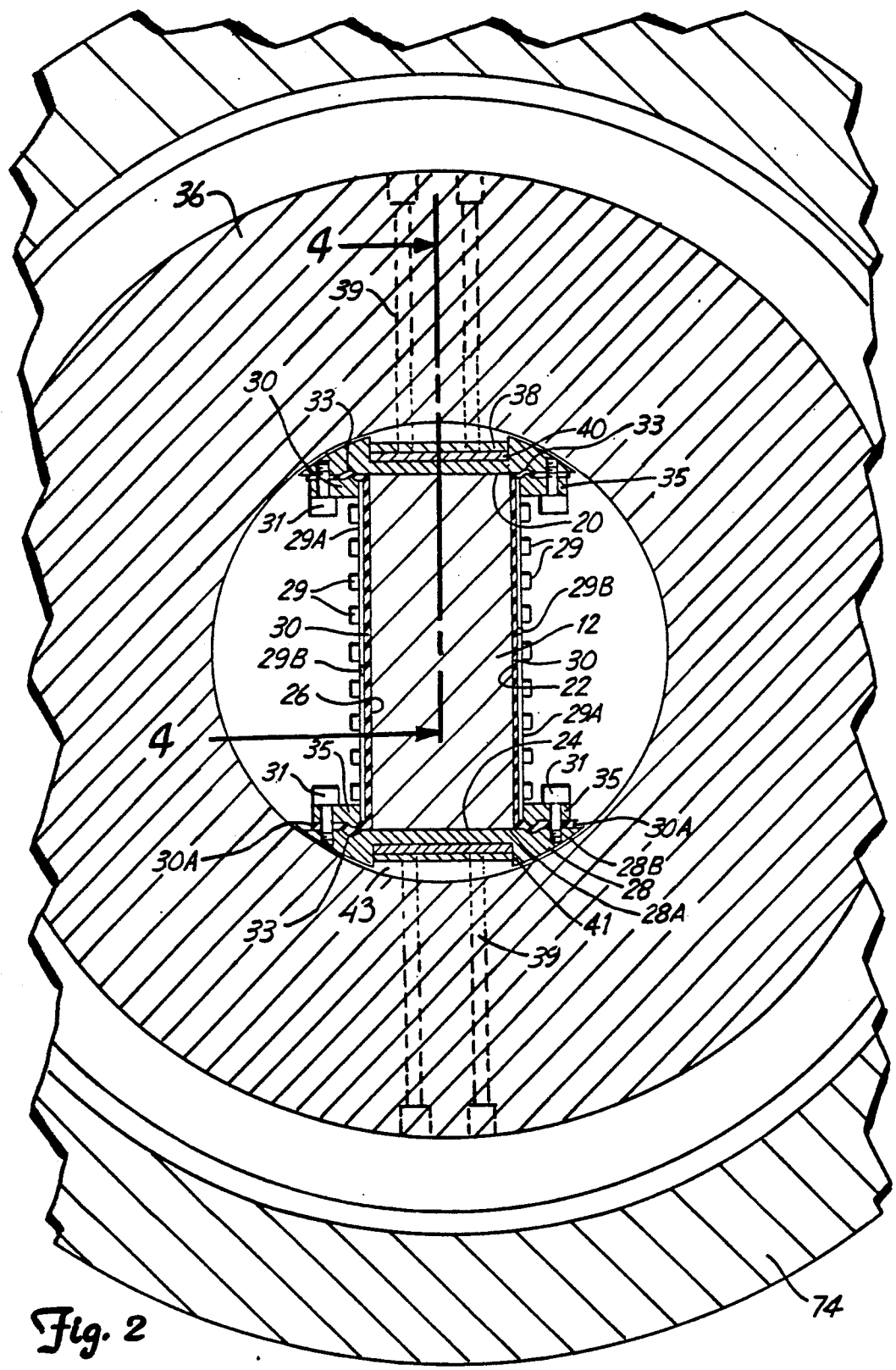
FIG. 2 is a sectional view taken on line 2—2 in FIG. 1.
Figure 3:
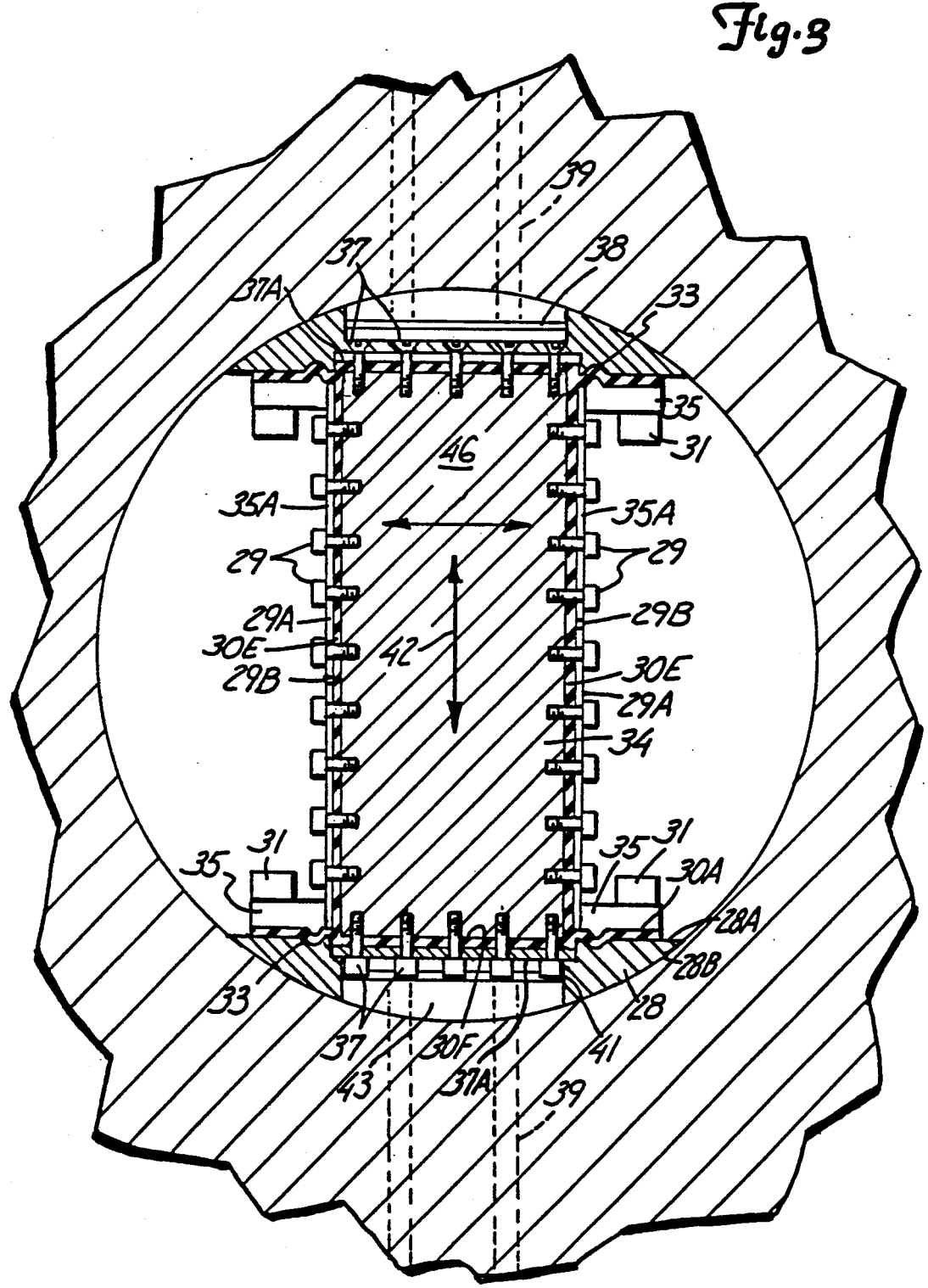
FIG. 3 is a sectional view taken on line 3—3 in FIG. 1.
Figure 4:
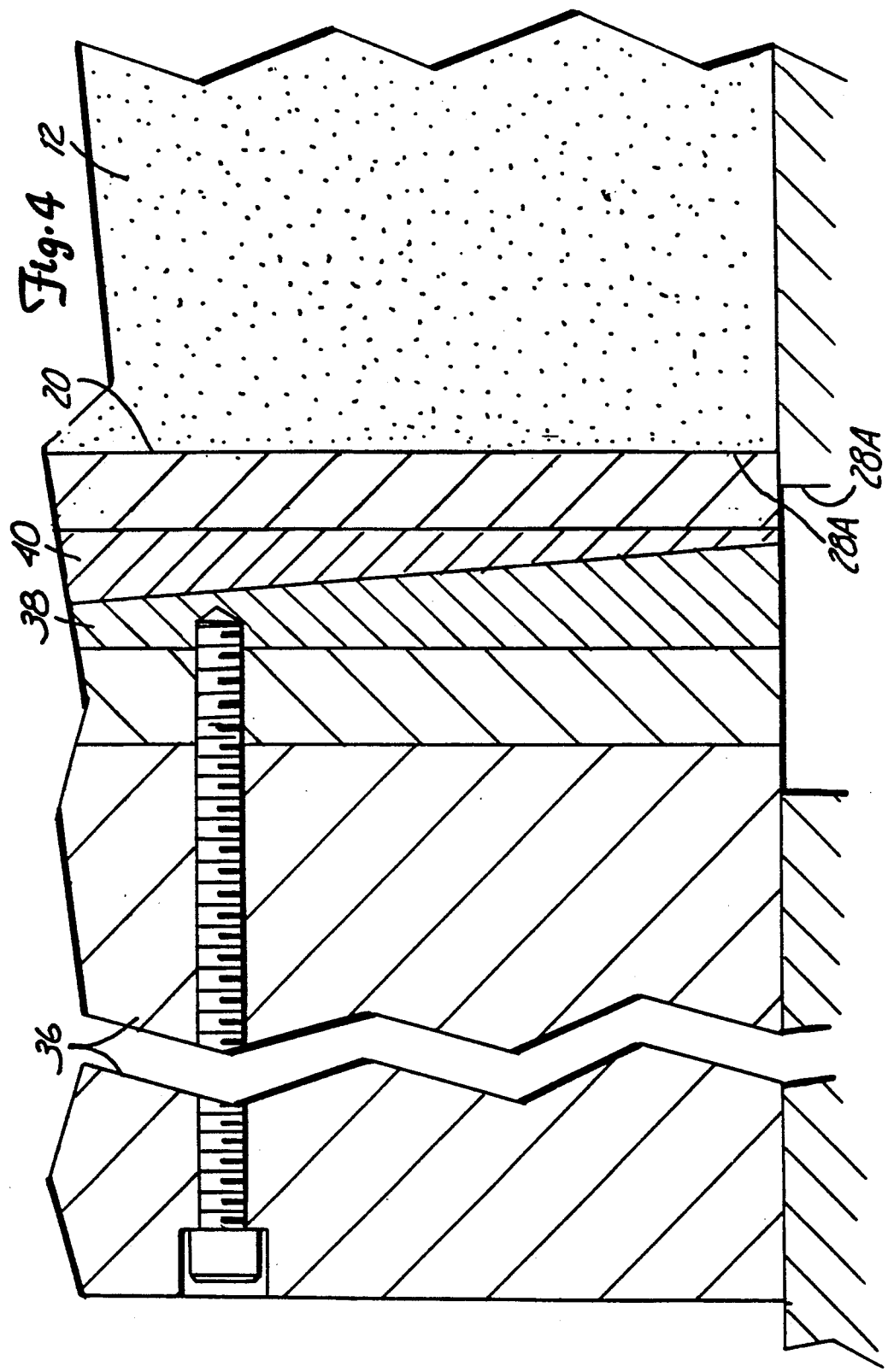
FIG. 4 is a fragmentary enlarged sectional view taken on line 4—4 in FIG. 2.

As illustrated in FIGS. 2 and 3, the bearing plates 28 include indentations or grooves 33 that extend the full height of the bearing plates 28 aiding in clamping and retaining the flanges 30A. The clamp strap 35 has a rib that forces a portion of the flange 30 into the indentation 33 and effects a seal along the edges of the specimen 12.

As illustrated in FIG. 1 and also FIG. 5, the membrane 30 is attached to the bottom support plate 32 and the top plate 34 and sealed all around openings 30D for the plates 32 and 34. The membrane side walls have flange portions 30E that extend above and below the sides 22, 26 of the specimen and also have seal flanges 30F above and below the openings 30B in the sleeve 30.

The flanges 30E of the sleeve 30 are clamped and sealed against the adjacent side surfaces of the bottom support plate 32 and the corresponding surfaces of the top plate 34 with clamp strips 29A and screws 29. The screws 29 thread directly into the side surface of the support plate 32 and top plate 34. The bottom support plate 32 has a boss portion that fits between flanges 30E and 30F as shown in FIGS. 1 and 5.

The flanges 30F of the sleeve 30 are clamped and sealed against the aligning side surfaces of the bottom support plate 32 and top plate 34 with clamp strips 37A and screws 37. These screws also thread into the boss portion of the bottom support plate 32 and into the top plate 34, as shown in FIG. 3. The membrane 30 tightly adheres to the top plate 34, the bottom plate 32 and to the bearing plates 28 such that the edges of the specimen 12 are sealed, so membrane 30 will prevent pressurized oil (as will be discussed later) from contacting the specimen 12. The strips 29A also can be split with a gap such as that shown at 29B between sections to permit some movement of the bearing plates 28 toward each other for fixing the specimen 12 in place as will be discussed later.

The bottom support plate 32 supports the first end surface 16 of the specimen 12, and a top plate 34 engages the second end surface 18 of the specimen 12. The specimen 12, plates 32 and 34 and bearing plates 28 are surrounded by a heavy wall cylindrical frame 36. The frame 36 forms a central opening and is fixed to an adapter sleeve 36A which is supported back to a load frame base through a housing 60.

The bearing plates 28 have flat side surfaces 28A, and curved outer surfaces 28B. The curved outer surfaces are made to conform to the central opening of the frame 36. The bearing plates each have a recess 4 formed in the surfaces 28A so that the recesses open toward the interior surface defining the opening in frame 36. A pair of spacers indicated at 43 are provided with part cylindrical outer surfaces that fit against the interior surface of the opening in frame 36, and have flat inner surfaces that are generally parallel to the adjacent side surfaces of the specimen, and also parallel to the inner surface of the recess in the bearing plates 28.

The recesses 41 receive portions of the spacers 43 as shown, and base wedge plates 38 are placed against the inner surfaces of the spacers 43 and held securely with respect to the frame 36 by bolts 39. The bolts 39 clamp the spacers 43 and the base wedge plates 38 securely with respect to the cylindrical frame without restraining the bearing plates 28. Each of the base wedge plates 38 are used in connection with a mating adjustment wedge plate 40 that is used for taking up any spacing between the specimen and the bearing plates by forcing the bearing plates toward the specimen under the wedging force. The bearing plates, therefore, bear directly against the specimen, and the wedge plates and spacers react forces and restrain movement of the specimen 12 to be tested in first lateral directions 42 which are indicated in FIG. 3 by the double arrow and are perpendicular to the central axis 14 indicated in FIG. 1. The gap 29B between sections of strips 29A will permit some tightening movement of the bearing plates 28 under action of the wedges 38, 40.

The wedge plates 38 and 40 and frame 36 provide a rigid form to resist extrusion or movement of the side surfaces 20 and 24 of specimen 12 in the first lateral directions 42. Adjustment wedge plates 40 are mated conventionally with the base wedge plates 38 with the adjustment wedge plates 40 being disposed between the base wedge plates 38 and the bearing plates 28. A layer of lubricant, including, but not limited to, stearic acid, is placed between the bearing plates 28 and the specimen 12 to minimize friction between the bearing plates 28 and the specimen 12.

The use of the adjustment wedge plates 40 are used to assure a snug and tight fit of the specimen 12 within the frame 36. The adjustment wedge plates 40 are preferably wedged between the base wedge plates 38 and the bearing plate 28 to urge the bearing plate 28 against the respective side surface 20, 24 of the specimen 12 and snugly hold the specimen 12 within the frame 36. The adjustment wedge plates 40 are generally trapezoidal-shaped in cross-section and are fitted together as a pair such that the sides of the adjustment wedge plates 40, are substantially parallel to the plane of the bearing plate 28. While any number of adjustment wedge plates 40 may be utilized, there generally are at least two such adjustment wedge plates 40 on each side of the specimen 12. The adjustment wedge plates 40 are of any desired thickness depending on the cut size of the specimen 12 relative to the spacing of the base wedge plates 38. The adjustment wedge plates 40 can have hardened steel surfaces.

The bearing plates 28 include a flat side surface 28A, a curved surface 28B, and a recessed area 41. The flat side surface 28A is positioned against the side surfaces 20, 24 of the specimen 12. The curved surface 28B is shaped such that the curved surface 28B rests against the inside surface of the cylindrical frame 36. The bearing plates 28 are attached to the frame 36 in a conventional manner and the recessed area 41 restrains the base wedge plates 38 and the adjustment wedge plates 40 from movement in second lateral directions 46 perpendicular to the first lateral direction 42.

The bearing plates 28 are preferably constructed of hardened steel. In addition, the flat side surface 28A of the bearing plates 28 has been polished in order to minimize friction between the specimen 12 and the flat side surface 28A.

The top plate 34 is attached to a linear slide assembly indicated generally at 48, which is a commercially available unit, that is made to provide a very low coefficient of friction sliding top support for the specimen 12. The specimen 12 thus can readily and easily slide in directions along the axis 50 of the linear slide assembly 48 (FIG. 1). As shown, the linear slide assembly 48 has a sliding movable member 52 mounted onto a rail 55 with suitable ball supports mounted in raceways formed in the rail and in the mating surface of the sliding member 52. Thus, the top plate 34 and the slide assembly 48 provides substantially friction free sliding movement in second lateral directions 46 parallel to the plane of the base wedge plates 38 and perpendicular to the supported first and second end surfaces 16, 18 of the specimen 12.

The specimen 12 is substantially unrestrained from shifting in the second lateral directions 46 perpendicular to the first lateral directions 42 and the central axis 14. Means 56 for loading the second end surface 18 are provided to move the top plate 34 toward the bottom support plate 32 along the central axis 14 of the specimen 12 until the specimen 12 fails in shear and at least two portions of such specimen 12 shift relative to each other in the second lateral directions 46.

A load cell 58 is provided to support the bottom support plate 32 relative to support sleeve 36A and a base 60 for measuring the load on the specimen 12 reacted to the bottom support plate 32. The base 60 is supported relative to the test frame which is used. The load cell 58 measures the load applied to the first end surface 16 of the specimen 12 being tested and can be used to determine the friction between the specimen 12 and its supports.

The means for loading 56 comprises an actuator 62 that loads the top plate 34 through an external load cell 59. A loading ram 64 acts on the top plate 34 through the linear slide assembly 48 fixed to the top plate 34.

In addition to monitoring the axial loads that are applied, using the load cells 58, 59, it is important to determine when the specimen 12 fails in compression along a shear plane from the axial load. In order to determine when and where failure occurs, a number of displacement sensors 68, 70, 71, 72 are mounted to sense shifting of first and second end surfaces 16, 18 of the specimen 12, and also to sense any shifting of the top plate 34 in direction along the axis 50 of the linear slide assembly 48. The movement of the top plate 34 in direction of the central axis 14 as the specimen 12 is loaded is also sensed by linear displacement sensors 72.

Figure 6:
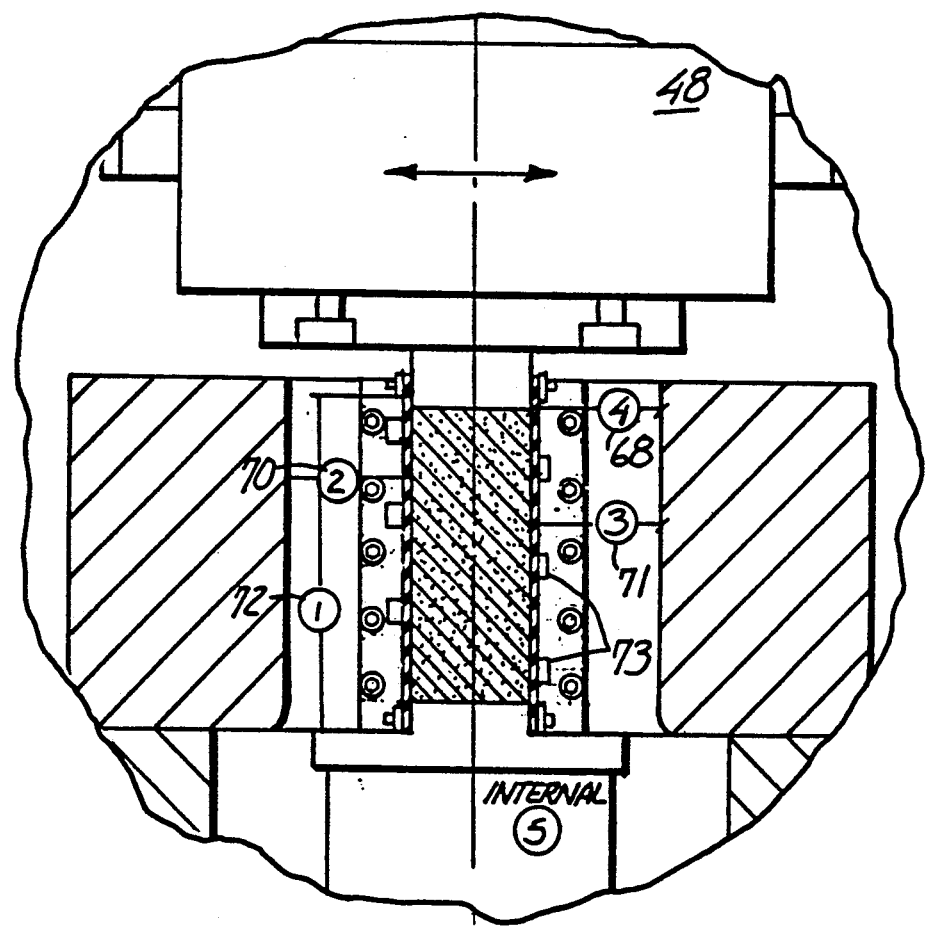
FIG. 6 is a vertical sectional view similar to FIG. 1 illustrating in detail the placement of the displacement sensors.

As illustrated in FIG. 6, a first displacement sensor 68 is provided for sensing displacements of the top plate 34 for movement along the axis 50 of the linear slide assembly 48. A pair of second linear displacement sensors 70, 71 are provided which engage each of the side surfaces 22, 26 of the specimen 12. The side surfaces 22, 26 that will shift when the specimen fails are generally perpendicular to the plane of the base wedge plates 38. The second displacement sensors 70, 71 are positioned at two different axially spaced locations to determine differential movements between at least two portions of the specimen 12 being tested. In addition, a third displacement sensor 72 is provided for measuring the displacement between the top plate 34 and the support plate 32 along the support axis 14. A plurality of acoustic emission sensors 73 are also placed at various points on the side surfaces 22, 26 to sense microseismic sources and to map failure of the specimen 12. A plurality of lead openings 77 in the support sleeve 36A is provided for the leads from the load cell 58, displacement sensors 70, 71 and 72 and the acoustic emission sensors 73 to pass through. The openings 77 are constructed such that pressure surrounding the specimen 12 will be maintained through means of a gasket or other sealing mechanism.

Tests are usually conducted with the entire specimen 12, and the loading assembly, including the base wedge plates 38, the support plate 32, and the linear slide assembly 48, as well as the cylindrical frame 36, inside a pressure vessel 74, which permits a hydrostatic pressure to be applied to sides 22, 26 of the specimen 12 to prevent failures which are not attributable to shear failures. The pressure vessel 74 is preferably a steel cylinder, which seats down onto a shoulder 76 on the base 78, and which is sealed by a suitable O-ring 80. The load is applied vertically with no tilting allowed. Slight misalignment of the load frame is compensated by adjustment of the upper plate 82, which is machined to allow for proper alignment and sealed by suitable O-ring 81. An upper plate 82 is used to seal the pressure vessel 74 in a known manner and then the vessel 74 can be filled with oil and placed under a pressure, for example in the range of up to approximately 200 atmospheres (approximately 3000 psi). The loading ram 64 fixed to the top plate 34 is slidably sealed with respect to the upper plate 82 of the vessel 74 so it can provide a load through the upper plate 82 in a conventional manner.

The pressure in the pressure vessel 74 can be regulated in a manner presently known and used for testing geomaterial samples, and does not form part of the present invention, in that it is conventionally done for testing purposes. A conduit 90 is provided for allowing a supply of oil or other fluid into the pressure vessel 74. In order to close the conduit 90, a threaded adapter 92 is threaded into a threaded aperture 94 located in the support sleeve 36A thereby sealing the conduit 90. A bleeder 96 is provided in upper plate 82 to allow the pressure of the oil or other fluid to be adjusted or released.

As the axial force along the central axis 14 increases, tending to axially compress the specimen 12, the amount of shifting of the specimen 12 in the longitudinal central axial direction 14 can be sensed by the third displacement sensor 72. Any tendency of the top plate 34 to slide laterally as the specimen 12 fails in shear will be sensed by the first displacement sensor 68 that has an indicator shaft which rests against an edge portion of the top support plate 34 to sense its movements in directions along the axis 50 of the support plate 54.

As the specimen 12 starts to fail along a shear plane, one portion of the specimen 12 will tend to shift laterally of its longitudinal central axis 14 relative to other portions in one of the second lateral directions 46. This shifting will be sensed by the second displacement sensors 70, 71. The shear plane failure at an angle with respect to the axis 14 is generally as shown in the prior art mentioned in the Background of the Invention. That prior art also discusses the types of tests and test theory involved. The upper and lower portions of the specimen 12 shift relative to each other when shear failure occurs.

The test loads can be carefully controlled, and the low friction slide assembly 48 insures that the loading of the specimen 12 will be unaffected by binding or friction loads of the top plate 34.

Although the present invention has been described with reference to preferred embodiments, workers skilled in the art will recognize that changes may be made in form and detail without departing from the spirit and scope of the invention.

What is claimed is:

1. A plane-strain apparatus for testing soft rock and concrete specimens, which have an unconfirmed compressive strength of less than 35 MPa, for failure under load in direction generally along a central axis of the specimen, for a specimen with first and second end surfaces, and four side surfaces, forming a generally rectangular prism cross section configuration, the apparatus comprising:
    a bottom support plate supporting the first end surface of the specimen;
    a top plate supporting the second end surface of the specimen;
    a rigid frame for restraining movement of the specimen to be tested, the specimen movement being restrained in first lateral directions perpendicular to the axis of loading, the specimen being loaded being substantially unrestrained from shifting in second lateral directions perpendicular to the first lateral directions;
    means for loading such specimen on the second end surface under a load directed toward the bottom support plate along the central axis of the specimen until such specimen fails in shear and at least two portions of such specimen shift in one of the second lateral directions; and
    wedges between the frame and the specimen for securing the specimen within the frame in the first lateral directions.

2. The apparatus as specified in claim 1 and a pair of bearing plates resting against a pair of opposite side surfaces of the specimen.

3. The apparatus as specified in claim 2 and a membrane covering the two portions of the specimen which shift in one of the second lateral directions, the membrane being secured to the top plate, the bottom support plate and the bearing plates.

4. The apparatus of claim 3 wherein the membrane comprises a sleeve.

5. The apparatus as specified in claim 3 wherein the membrane includes side walls, the side walls having flange portions that extend above and below the sides of the specimen.

6. The apparatus of claim 5 wherein the membrane is left open with openings at the side surfaces of the specimen whereby the bearing plates engage these side surfaces.

7. The apparatus of claim 6 wherein the sleeve includes a plurality of flanges integrally formed as part of the sleeve, the flanges extending outwardly from the specimen to rest on surfaces of the bearing plates, the top plate and the bottom support plate, surrounding the specimen.

8. The apparatus of claim 7 wherein a clamp strap is mounted over each of the flanges and a plurality of screws clamp the strap against the flanges after the membrane is stretched taut.

9. The apparatus of claim 8 wherein the straps are made in section with a gap between two sections to permit shifting of the specimen when the specimen is loaded.

10. The apparatus as specified in claim 1 and low friction linear slide means for mounting the top plate for movement along a linear support substantially parallel to the planes of the wedges.

11. The apparatus as specified in claim 10 and first displacement sensor means for sensing displacements of the top plate for movement along the axis of the linear slide means.

12. The apparatus as specified in claim 11 and second displacement sensor means engaging at least one side surface of a specimen to be tested that is generally perpendicular to the plane of the wedges at two different axially spaced locations to determine differential movements between at least two portions of a specimen being tested.

13. The apparatus as specified in claim 12 and third displacement sensor means for measuring the displacement between the top plate and the bottom support plate along the support axis.

14. The apparatus as specified in claim 10 and a load cell supported on the bottom support plate for measuring the load on a specimen transferred to the bottom support plate.

15. The apparatus as specified in claim 14 and a second primary load cell for measuring the load applied to a first end of a specimen being tested, the friction that is present between the specimen and the wedges thereby being capable of being determined by measuring the differential in loads from the load cell associated with the support plate and the second primary load cell.

16. The apparatus as specified in claim 1 and a pressure vessel surrounding the apparatus whereby the pressure vessel is filled with liquid and placed under a pressure.

17. The apparatus as specified in claim 1 and a plurality of acoustic emission sensors are placed at various points on the two portions of the specimen which shift in one of the second lateral directions to sense microseismic sources and to map failure of the specimen.

18. A plane-strain apparatus for testing soft rock and concrete specimens, which have an unconfined compressive strength of less than 35 MPa, for failure under load in direction generally along a central axis of the specimen, for a specimen with first and second end surfaces, and at least two parallel side surfaces, the apparatus comprising:
    a support plate supporting the first end surface of the specimen;
    a rigid frame for restraining movement of the specimen to be tested, the specimen movement being restrained in first lateral directions perpendicular to the axis of loading, the specimen being loaded being substantially unrestrained from shifting in second lateral directions perpendicular to the first lateral directions; and means for loading specimen on a second end surface under a load directed toward the support plate along the central axis of the specimen until such specimen fails; and a plurality of wedges between the frame and the specimen for restraining deformation of the specimen in the first lateral direction.

* * * * *

UNITED STATES PATENT AND TRADEMARK OFFICE
CERTIFICATE OF CORRECTION

PATENT NO.  : 5,063,785
DATED       : November 12, 1991
INVENTOR(S) : Joseph F. Labuz et al.

It is certified that error appears in the above-identified patent and that said Letters Patent is hereby corrected as shown below:

Col. 9, line 6, after "loading", insert --such--.

Signed and Sealed this

Twenty-third Day of March, 1993

*Attest:*

STEPHEN G. KUNIN

*Attesting Officer*       *Acting Commissioner of Patents and Trademarks*